(12) United States Patent
Battaglia

(10) Patent No.: US 10,220,194 B2
(45) Date of Patent: Mar. 5, 2019

(54) DUAL CHAMBER APPLICATOR

(71) Applicant: Jaleva Pharmaceuticals, LLC, San Diego, CA (US)

(72) Inventor: Alex Battaglia, La Jolla, CA (US)

(73) Assignee: ADVANCED RESIN THERAPEUTICS, INC., San Diego, CA (US)

(*) Notice: Subject to any disclaimer, the term of this patent is extended or adjusted under 35 U.S.C. 154(b) by 0 days.

(21) Appl. No.: 14/647,579

(22) PCT Filed: Nov. 26, 2013

(86) PCT No.: PCT/US2013/071990
§ 371 (c)(1),
(2) Date: May 27, 2015

(87) PCT Pub. No.: WO2014/085445
PCT Pub. Date: Jun. 5, 2014

(65) Prior Publication Data
US 2015/0306362 A1    Oct. 29, 2015

Related U.S. Application Data

(60) Provisional application No. 61/730,665, filed on Nov. 28, 2012.

(51) Int. Cl.
*B65B 5/04* (2006.01)
*B65B 7/02* (2006.01)
(Continued)

(52) U.S. Cl.
CPC .......... *A61M 35/003* (2013.01); *A61B 50/30* (2016.02); *A61M 31/00* (2013.01);
(Continued)

(58) Field of Classification Search
CPC .. A61M 35/003; A61M 31/00; A61M 35/006; A61B 50/30; B65B 5/04; B65B 7/02; B65B 55/02
See application file for complete search history.

(56) References Cited

U.S. PATENT DOCUMENTS 3,764,796 A    10/1973    Gilliam et al.
3,813,534 A    5/1974    Gilliam
(Continued)

FOREIGN PATENT DOCUMENTS

WO    WO-01/74321 A2    10/2001
WO    WO-2005/009386 A2    2/2005
(Continued)

OTHER PUBLICATIONS

International Search Report dated Mar. 14, 2014 in application No. PCT/US2013/071990.
(Continued)

*Primary Examiner* — Lauren P Farrar
(74) *Attorney, Agent, or Firm* — Foley & Lardner LLP

(57) ABSTRACT

A dual chamber applicator includes an elongated tube having a sealed end and an open end, a first ampoule disposed in the elongated tube and containing a first composition including a pharmaceutically active agent and optionally a first volatile solvent, water, or a combination thereof, a second ampoule disposed in the elongated tube and containing a second composition including a resin based tincture, a second volatile solvent and water, and an applicator device provided at the open end of the elongated tube. The first composition is configured to combine with the second composition within the elongated tube to form a medicine to be delivered to a mucosal site or a skin site. The applicator device is configured to control flow of the medicine out of
(Continued)

the open end of the elongated tube and deliver the medicine via topical, transdermal or transmucosal delivery.

25 Claims, 2 Drawing Sheets

(51) Int. Cl.
    *A61B 50/30*     (2016.01)
    *A61F 13/40*     (2006.01)
    *A61M 31/00*     (2006.01)
    *A61M 35/00*     (2006.01)
    *B65B 55/02*     (2006.01)

(52) U.S. Cl.
    CPC ............. *A61M 35/006* (2013.01); *B65B 5/04* (2013.01); *B65B 7/02* (2013.01); *B65B 55/02* (2013.01)

(56) References Cited

U.S. PATENT DOCUMENTS

| | | |
|---|---|---|
| 4,707,450 A | 11/1987 | Nason |
| 5,039,618 A | 8/1991 | Stone |
| 5,171,149 A | 12/1992 | Alpert |
| 5,278,075 A | 1/1994 | Stone |
| 5,330,917 A | 7/1994 | Stone |
| 5,364,792 A | 11/1994 | Stone |
| 5,550,061 A | 8/1996 | Stone |
| 5,980,055 A | 11/1999 | Palmer et al. |
| 6,043,097 A | 3/2000 | Dumitrescu et al. |
| 6,440,371 B1 | 8/2002 | Dumitrescu et al. |
| 6,478,191 B1 | 11/2002 | D'Alessio et al. |
| 6,899,897 B2 | 5/2005 | Battaglia |
| 7,631,645 B2 | 12/2009 | Gayton et al. |
| 8,648,082 B2 | 2/2014 | Battaglia et al. |
| 8,709,439 B2 | 4/2014 | Battaglia |
| 8,846,092 B2 | 9/2014 | Battaglia et al. |
| 2002/0022816 A1* | 2/2002 | Knox .................. A61K 9/0031 604/385.18 |
| 2004/0191274 A1 | 9/2004 | Grayson et al. |
| 2004/0200754 A1* | 10/2004 | Hagemeier ........... A61F 9/0017 206/570 |
| 2005/0049550 A1 | 3/2005 | Kirchhofer et al. |
| 2005/0072442 A1* | 4/2005 | Licari .................... A45D 19/02 132/112 |
| 2008/0041739 A1 | 2/2008 | Gayton et al. |
| 2008/0170904 A1* | 7/2008 | Bayly .................... A45D 34/04 401/265 |
| 2008/0195040 A1* | 8/2008 | Clark ............... A61B 17/00491 604/87 |
| 2008/0286299 A1* | 11/2008 | Battaglia .............. A61K 9/0014 424/195.18 |
| 2009/0004252 A1 | 1/2009 | Lowndes et al. |
| 2009/0152295 A1 | 6/2009 | May et al. |
| 2011/0137339 A1 | 6/2011 | Stenton |
| 2011/0208136 A1* | 8/2011 | Sollingen ............ A61M 35/003 604/290 |
| 2011/0281771 A1 | 11/2011 | Chernokalskaya et al. |
| 2011/0284583 A1 | 11/2011 | Fazzolari |
| 2012/0074001 A1 | 3/2012 | Genosar |
| 2014/0371210 A1 | 12/2014 | Battaglia |
| 2015/0051200 A1 | 2/2015 | Battaglia et al. |

FOREIGN PATENT DOCUMENTS

| | | |
|---|---|---|
| WO | WO-2005/065640 A1 | 7/2005 |
| WO | WO-2008/156559 A2 | 12/2008 |
| WO | WO-2013/056159 A1 | 4/2013 |

OTHER PUBLICATIONS

International Search Report dated Feb. 20, 2014 in application No. PCT/US2013/064556.
Supplementary European Search Report dated Jul. 28, 2016, received in corresponding European application No. 13859213.4, 10 pages.
European Search Report dated May 10, 2016 in application No. EP 13845634.8, 3 pages.
U.S. Office Action dated Dec. 9, 2016 in U.S. Appl. No. 14/434,857.
U.S. Office Action on U.S. Appl. No. 14/434,857 dated Sep. 20, 2017.

* cited by examiner

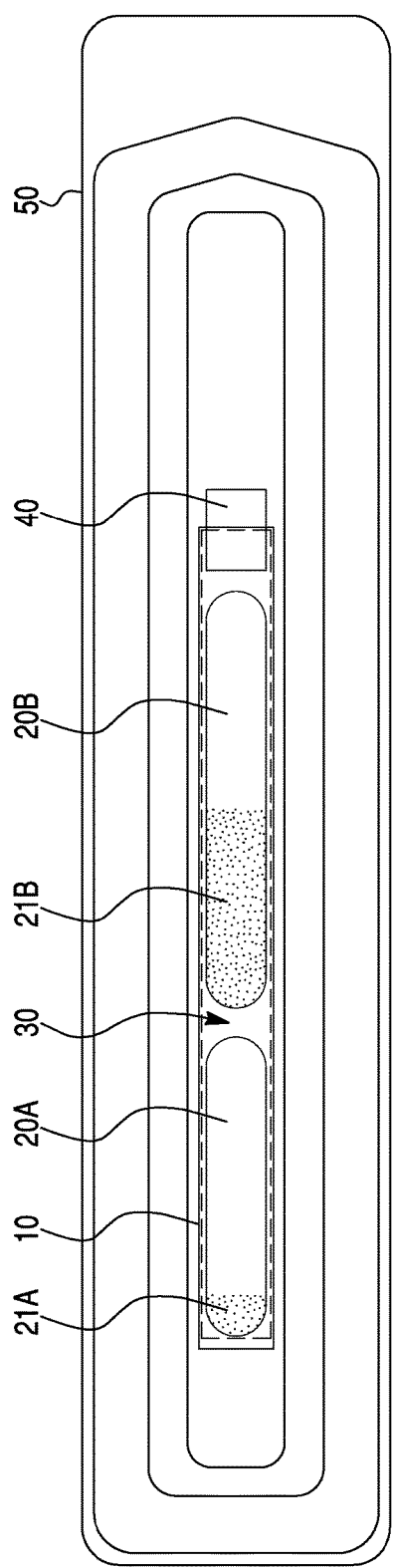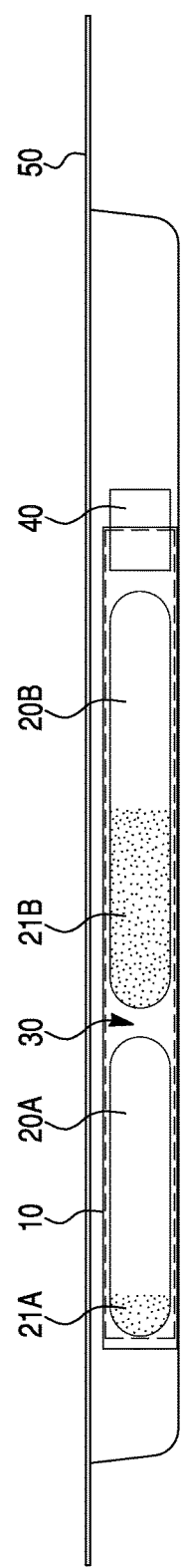

DUAL CHAMBER APPLICATOR

CROSS REFERENCE TO RELATED APPLICATIONS

The present application is a U.S. National Stage of International Application No. PCT/US2013/071990 filed on Nov. 26, 2013, which claims benefit of U.S. Provisional Patent Application No. 61/730,665 filed on Nov. 28, 2012, the entire disclosures of all of which are incorporated herein by reference.

BACKGROUND

Field of Embodiments

The disclosed embodiments relate generally to dual chamber applicators containing pharmaceutical compositions for topical, transdermal or transmucosal use, and methods of using dual chamber applicators to effect topical, transdermal or transmucosal delivery of a pharmaceutically active agent.

Background

Applicators containing pharmaceutical compositions for topical, transdermal or transmucosal use are known, but there continues to be a need for applicators for pharmaceutical compositions that are unstable or that include one or more unstable components. For example, resin tinctures comprising a pharmaceutically active agent, alcohol and resin may suffer from instability, such as may be associated with specific active agents (such as bacitracin or chlorhexidine gluconate) that become unstable when they are mixed in an alcoholic solution that also includes a resin, such as benzoin or mastic gum. For example, the pharmaceutically active ingredient, may (1) fail to dissolve, (2) precipitate, or (3) break down over time once placed into an alcoholic solution that also includes a resin. There remains a need for applicators for such compositions.

SUMMARY

One embodiment relates to a dual chamber applicator including an elongated tube having a sealed end and an open end, a first ampoule disposed in the elongated tube and containing a first composition comprising a pharmaceutically active agent and optionally a first volatile solvent, water, or a combination thereof, a second ampoule disposed in the elongated tube and containing a second composition comprising a resin based tincture, a second volatile solvent and water, and an applicator device provided at the open end of the elongated tube. The first composition configured to combine with the second composition within the elongated tube to form a medicine to be delivered to a mucosal site or a skin site. The applicator device is configured to control flow of the medicine out of the open end of the elongated tube and deliver the medicine via topical, transdermal or transmucosal delivery.

Another embodiment relates to a method for delivery of medicine to a mucosal site or a skin site using a dual chamber applicator including an elongated tube having a sealed end and an open end, a first ampoule and a second ampoule disposed within the elongated tube, the first ampoule containing a first composition comprising a pharmaceutically active agent and optionally a first volatile solvent, water, or a combination thereof and the second ampoule containing a second composition comprising a resin based tincture, a second volatile solvent and water, and an applicator device provided at the open end of the elongated tube. The method includes deforming the elongated tube to crush the first and second ampoules to release the first composition and the second composition into an interior of the elongated tube, shaking the dual chamber applicator such that the first composition and the second composition combine to form a medicine to be delivered to the mucosal site or the skin site, and applying the medicine topically, transdermally or transmucosally via the applicator device.

BRIEF DESCRIPTION OF THE DRAWINGS

The disclosure will become more fully understood from the following detailed description, taken in conjunction with the accompanying figures, in which:

FIG. 3 is a top view of the dual chamber applicator according to the embodiment of FIG. 1 within a blister pack.

FIG. 4 is a side view of the dual chamber applicator according to the embodiment of FIG. 1 within the blister pack as shown in FIG. 3.

DETAILED DESCRIPTION

Overview

Described herein are a dual chamber applicator and methods of using it to effect topical, transdermal or transmucosal delivery of an active agent on the skin, nail or oral mucosa. In particular, as described in more detail below, described herein is a dual chamber applicator that is particularly advantageous when used with resin tincture compositions for topical, transdermal or transmucosal use, as well as methods for using the dual chamber applicators to effect topical, transdermal or transmucosal delivery of a pharmaceutically active agent. The pharmaceutically active agent is stored within an ampoule provided within the dual chamber applicator and prevented from mixing with a resin until the applicator is ready to be used. Storing the pharmaceutically active agent in such a manner increases stability of the pharmaceutically active agent. Additionally or alternatively, in some embodiments, the pharmaceutically active agent does not precipitate out of solution or break down over time. Thus, medicines or compositions made by these methods are convenient and effective for the topical, transdermal or transmucosal delivery of pharmaceutically active agents. The configuration of the dual chamber applicator may safely and dramatically improve the efficacy of a medicine delivered to a mucosal site or a skin site by applying a transparent, medicated film that reduces the number of applications required for an active ingredient.

In accordance with some embodiments, the pharmaceutical compositions described herein provide improved delivery of pharmaceutically active agents that are less soluble in organic solvents (such as alcohols), and other pharmaceutically active agents that heretofore have not been able to be stably formulated in resin tinctures.

Figure 1:
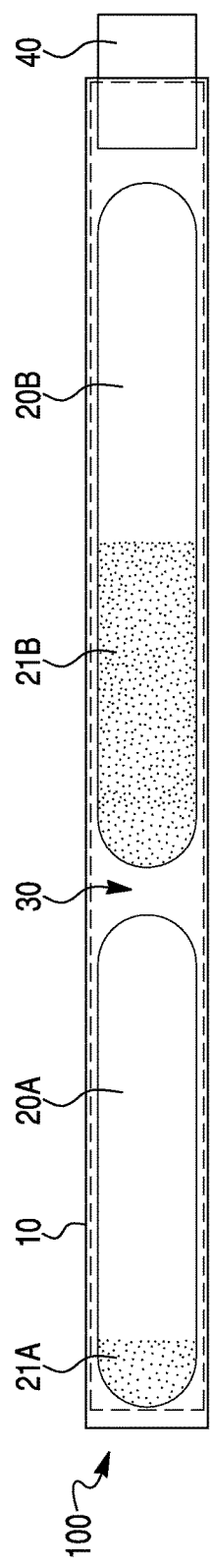
FIG. 1 is a side view of a dual chamber applicator according to an illustrative embodiment.
Figure 2:
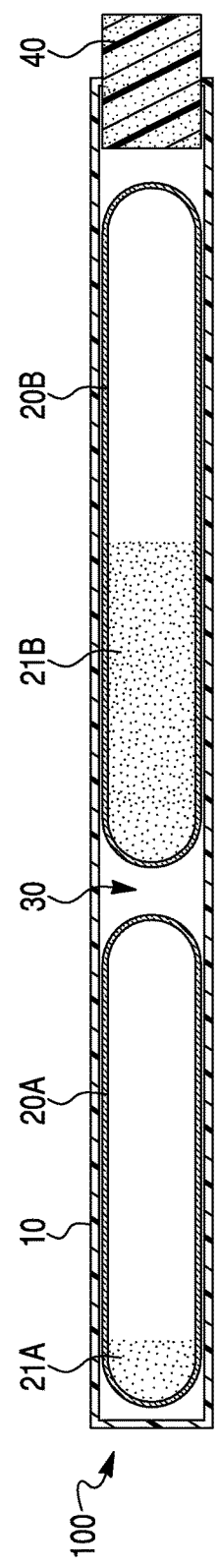
FIG. 2 is a cross-sectional view of the dual chamber applicator according to the embodiment of FIG. 1.

Referring to FIGS. 1-4, an embodiment of a dual chamber applicator 100 includes an applicator tube 10 containing a first ampoule 20A and a second ampoule 20B within an interior 30 of the applicator tube 10, and an applicator device 40 configured to control flow of a pharmaceutical composition (i.e., medicine) out of an open end of the applicator device 40. The first ampoule 20A contains a first composition 21A and the second ampoule 20B contains a second composition 21B.

Applicator Tube

In one embodiment, the applicator tube 10 has a structure that permits appropriate mixing of compositions for application. The applicator tube 10 may be an elongated tube composed of a flexible material. In one example, the flexible material may be a clear, butyrate plastic tubing, for example, Eastman Tenite Butyrate (575E-37200-10). The applicator tube 10, however, may be composed of other suitable materials, such as other plastics, provided that the material selected is capable of being sterilized. The applicator tube 10 typically is of a suitable size to allow the dual chamber applicator 100 to be easily held within a hand of a user.

The applicator tube 10 may be a hollow, elongated tube having a sealed end and an open end. The open end of the applicator tube 10 may receive an applicator device 40, which will be described in further detail below. Walls of the applicator tube 10 may define an interior or a chamber 30 (see FIG. 2) in which the first and second compositions 21A, 21B may be mixed to form a pharmaceutical composition (i.e., medicine). In some embodiments, the applicator tube 10 has an outer diameter of approximately 8 mm and a length of approximately 75 mm from a sealed, first end of the applicator tube 10 to an open, second end of the applicator tube 10. In other embodiments, the applicator tube 10 has an outer diameter of approximately 10 mm or less and a length of approximately 99.3 mm or less from a sealed, first end of the applicator tube 10 to an open, second end of the applicator tube 10. In some embodiments, the applicator tube 10 can have an inner diameter (i.e., a diameter of the interior 30) of approximately 0.06 inches (1.524 mm) or more and an outer diameter of approximately 6 inches (152.4 mm) or less.

The flexibility of the applicator tube 10 and the thickness of the walls of the applicator tube 10 typically are configured to respectively allow the ampoules 20A, 20B to be ruptured or crushed by deformation of the applicator tube 10, while not allowing portions of the ampoules 20A, 20B to pierce or rupture the applicator tube 10. In embodiments in which the applicator tube 10 is composed of Eastman Tenite Butyrate (575E-37200-10), the tensile stress at yield of the applicator tube 10 is approximately 33.1 MPa (4800 psi), while the tensile stress at break of the applicator tube 10 is approximately 32.4 MPa (6300 psi). In use of the dual chamber applicator 100, the applicator tube 10 may not be pierced or ruptured.

Ampoules

The first ampoule 20A is configured to hold the first composition 21A and the second ampoule 20B is configured to hold the second composition 21B in a stable manner for transport, while being capable of being readily ruptured or crushed, when desired, within the interior 30 of the applicator tube 10 such that the first and second compositions 21A and 21B may be mixed to form a pharmaceutical composition (i.e., medicine) to be delivered topically, transdermally or transmucosally. Each of the first and second ampoules 20A and 20B may be a sealed container having walls that define a hollow interior (see FIG. 2) configured to hold the first or second composition 21A, 21B in a stable manner.

In one embodiment, the first ampoule 20A and the second ampoule 20B provide separate reservoirs for the compositions. Also, they typically are non-concentric. As used in this application, "non-concentric" means that the first ampoule 20A is not disposed within the second ampoule 20B, and the second ampoule 20B is not disposed within the first ampoule 20A. Instead, the first and second ampoules 20A and 20B are separate and independent of each other. This configuration is selected for sterility and crushability purposes.

The first and the second ampoules 20A and 20B can be glass ampoules composed, for example, of Type I borosilicate glass tubing such as Kimble N-51A. In other embodiments, the first and second ampoules 20A and 20B may be composed of other suitable materials, such as certain plastics, provided that the material selected is capable of being sterilized and crushed to release the contents of the ampoule. In one embodiment, the first and second ampoules 20A and 20B may be the same size. The thicknesses of the first and second ampoules 20A and 20B typically are configured to respectively allow the ampoules 20A, 20B to be ruptured by deformation of the applicator tube 10 while not allowing portions of the ampoules 20A, 20B to pierce or rupture the applicator tube 10. For example, the first and second ampoules 20A and 20B may each have a wall thickness of approximately 0.20 mm±0.02 mm and an outer diameter of approximately 7.0 mm±0.2 mm. In some embodiments, the first and second ampoules 20A and 20B may each have a length, for example, of approximately 47.5 mm. In other embodiments, the first and second ampoules 20A and 20B may each have a length of approximately 51.3 mm. In some embodiments, the first and second ampoules may each have a fill volume of approximately 0.66 mL. In other embodiments, the first and second ampoules 20A and 20B may each have a fill volume of approximately 0.94 mL. In other embodiments, the first and second ampoules 20A and 20B may each have a fill volume of approximately 1.02 mL. The diameters, lengths and fill volumes of the first and second ampoules 20A and 20B can be determined by the skilled artisan in order to obtain the desired concentrations of the components of the first and second compositions 21A and 21B in the pharmaceutical composition to be delivered to the mucosal site or the skin site, and to obtain the desired viscosity of the final pharmaceutical composition.

In other embodiments, the first and second ampoules 20A and 20B may have different lengths and/or diameters in order to change a fill volume of the ampoule. In a preferred embodiment, the second ampoule 20B is larger than the first ampoule 20A. For example, the first ampoule 20A may have a length less than 47.5 mm and a fill volume less than 0.94 mL, while the second ampoule 20B may have a length greater than or equal to 47.5 mm and a fill volume greater than or equal to 0.94 mL, such as a length of 51.3 mm and a fill volume of 1.02 mL. In another example, the first ampoule 20A may have a fill volume less than 0.66 mL, while the second ampoule 20B may have a fill volume greater than or equal to 0.66 mL. In other embodiments, the first ampoule 20A may be larger than the second ampoule 20B. By making one of the first and second ampoules 20A and 20B larger than the other of the first and second ampoules 20A and 20B, it is possible to change a ratio of the first and second compositions 21A and 21B in the pharmaceutical composition to be delivered to the mucosal site or skin site. The first and second ampoules 20A and 20B may be arranged in series (as illustrated in FIGS. 1-4) or in parallel (not illustrated) within the applicator tube 10.

While referred to herein as ampoules, it is to be understood that they can be any suitable device that provides the desired structure that provides a reservoir for transport while permitting rupture for mixing.

Applicator Device

The applicator device 40 is disposed at the open end of the applicator tube 10. The applicator device 40 is in fluid communication with the interior 30 of the applicator tube 10. The applicator device 40 may be configured to allow passage of the pharmaceutical composition to permit its application, while simultaneously preventing passage of the portions of the ampoules 20A, 20B. The applicator device 40 may be a porous structure. For example, the applicator device 40 may be composed of Airweave (100% polyester stitch bonded non-woven) and 3/16" polyester polyurethane foam or polyolefin. In some embodiments, the applicator device 40 is a sponge tip. To prevent leakage, the applicator device 40 may be cut and sealed with cross-linked polyurethane adhesive within the open end of the applicator tube 10.

The applicator device 40 is configured to control flow of the pharmaceutical composition or medicine out of the open end of the applicator tube 10. For example, the porous structure of the applicator device 40 may sufficiently inhibit flow to allow mixing of the pharmaceutically active agent and the resin within the interior 30 of the applicator tube 10 to form the pharmaceutical composition, without allowing the pharmaceutical composition to freely flow out of the dual chamber applicator 100. However, the applicator device 40 can be configured to allow some of the pharmaceutical composition to flow through the porous structure of the applicator device 40 such that the user can, for example, topically swab the pharmaceutical composition onto a wound. In one embodiment, the amount of pharmaceutical composition configured to flow through the porous structure of the applicator device is greater than or equal to 300 μL in order to provide a sufficient amount of pharmaceutical composition to cover a mucosal site or a skin site.

The amount of pharmaceutical composition capable of flowing through the porous structure of the applicator device 40 may be controlled by altering a size of the pores in the porous structure of the applicator device 40. For example, a pore size of the porous structure may be small enough such that during the flow of the pharmaceutical composition or medicine through the applicator device 40, the applicator device 40 may filter pieces of the first and second ampoules 20A and 20B (e.g., broken glass or plastic) and any particulates from the resin that did not dissolve into solution. For example, the applicator device 40 may have an average pore size ranging from approximately 1 μm to 1 mm, more preferably from approximately 1 μm to 100 μm.

The average pore size of the applicator device 40 may vary depending on a viscosity of the pharmaceutical composition. In a preferred embodiment, the applicator device 40 has an average pore size of approximately 1 μm to 100 μm and the pharmaceutical composition has a viscosity of approximately 10-30 centipoise (cP). When the pharmaceutical composition has a viscosity higher than 7 cP, the average pore size of the applicator device 40 is generally increased. For example, an applicator device 40 having an average pore size of approximately 40 μm to 300 μm, more preferably approximately 60 μm to 125 μm, is used in conjunction with a pharmaceutical composition having a viscosity of approximately 30 cP to 500 cP, more preferably, approximately 35 cP to 350 cP, and most preferably approximately 50 cP to 200 cP or approximately 60 cP to 140 cP at 25° C. The applicator device 40 may have a pore volume of less than or equal to 80 percent, preferably between approximately 20-60 percent.

The amounts of the first composition 21A and the second composition 21B (discussed in further detail below) and the pore size of the applicator device 40 can be determined by the skilled artisan in order to produce a pharmaceutical composition having the desired viscosity.

Contents of the Ampoules

The first and second ampoules 20A and 20B may contain a resin, a liquid or a powder. Contents of the first and second ampoules 20A and 20B may be the same or different. In specific embodiments, the first ampoule 20A contains a first composition 21A comprising or consisting of a pharmaceutically active agent and optionally a first volatile solvent and/or water, and the second ampoule 20B contains a second composition 21B comprising a resin, a second volatile solvent, and water.

Pharmaceutically Active Agent

As the pharmaceutically active agent, any pharmaceutically active agent can be used. In specific embodiments, the pharmaceutically active agent is topically active or capable of transdermal or transmucosal delivery. In specific embodiments, the pharmaceutically active agent is hydrophilic. In specific embodiments, the pharmaceutically active agent is insoluble or poorly soluble or becomes unstable when mixed in an alcoholic solution that also includes a resin, such as benzoin or mastic gum. For example, such pharmaceutically active agents may (1) fail to dissolve, (2) precipitate, or (3) break down over time once placed into an alcoholic solution that also includes a resin. For example, the pharmaceutically active agent may be one that heretofore has not been capable of being stably formulated in a resin tincture.

In one embodiment, the first ampoule 20A may consist of only the pharmaceutically active agent. In other embodiments, the first ampoule 20A may contain a first composition 21A comprising the pharmaceutically active agent and optionally, a first volatile solvent and/or water. In some embodiments, more than one pharmaceutically active agent can be included in the first composition 21A. In specific embodiments, two pharmaceutically active agents are included in the first composition 21A. In specific embodiments, three or more pharmaceutically active agents are included in the first composition 21A.

In the description that follows, specific pharmaceutically active agents are disclosed. It is to be understood that pharmaceutically acceptable salts, esters, and other pharmaceutically acceptable forms of the listed active agents (including prodrugs) are included in the disclosure.

In some embodiments, the pharmaceutically active agent may comprise bacitracin, polymyxin, chlorhexidine gluconate, fentanyl, retinoic acid (Retin-A), zolmitriptan, sumatriptan, naratriptan, rizatriptan or lorazepam. In other embodiments, the pharmaceutically active agent may comprise zyrtec (cetirizine), loratadine, or ciprofloxacin. In other embodiments, the pharmaceutically active agent is selected from the group consisting of nicotine, scopolamine, lidocaine, benzocaine, ketorolac, ibuprofen, ketoprofen, flurbiprofen, naproxen, astemizole, terfenadine, cimetidine, testosterone, retin-A. In other embodiments, the pharmaceutically active agent is selected from the group consisting of ondansetron, granisetron, zolmitriptan, dihydroergotamine, sumatriptan, rizatriptan, fentanyl, cocaine, alprazolam, clonazepam, lorazepam, diazepam, estazolam, apomorphine, risperidone, buprenorphine, naloxone, flumazenil, tadalafil, vardenafil, sildenafil, sildenafil mesylate, dolasetron, palonsetron, triazolam, naratriptan, diclofenac, etololac, meclofenamate, indocin, meloxicam, nabumetone, oxaprozin, prioxicam, sulindac, tolmetin, celecoxib, loratadine, desloratidine, cetirizine, morphine, hydromorphine, levorphanol, meperidine, oxycodone, oxymorphone, propanolol, calcitriol, and methylphenidate. In some embodiments, the pharmaceutically active agent is mupirocin.

In specific embodiments, the first composition 21A does not include glycerin.

In some embodiments, the pharmaceutically active agent is not chlorhexidine gluconate, and the pharmaceutical composition does not include chlorhexidine gluconate.

In some embodiments, the pharmaceutically active agent is not nicotine, and the pharmaceutical composition does not include nicotine.

In specific embodiments, the active agent is scopolamine, while in other specific embodiments the active agent is not scopolamine In specific embodiments, the active agent is ondansetron, while in other specific embodiments the active agent is not ondansetron. In specific embodiments, the active agent is granisetron, while in other specific embodiments the active agent is not granisetron. In specific embodiments, the active agent is zolmitriptan, while in other specific embodiments the active agent is not zolmitriptan. In specific embodiments, the active agent is dihydroergotamine, while in other specific embodiments the active agent is not dihydroergotamine. In specific embodiments, the active agent is sumatriptan, while in other specific embodiments the active agent is not sumatriptan. In specific embodiments, the active agent is rizatriptan, while in other specific embodiments the active agent is not rizatriptan. In specific embodiments, the active agent is fentanyl, while in other specific embodiments the active agent is not fentanyl. In specific embodiments, the active agent is lidocaine, while in other specific embodiments the active agent is not lidocaine. In specific embodiments, the active agent is cocaine, while in other specific embodiments the active agent is not cocaine. In specific embodiments, the active agent is benzocaine, while in other specific embodiments the active agent is not benzocaine. In specific embodiments, the active agent is alprazolam, while in other specific embodiments the active agent is not alprazolam. In specific embodiments, the active agent is clonazepam, while in other specific embodiments the active agent is not clonazepam. In specific embodiments, the active agent is lorazepam, while in other specific embodiments the active agent is not lorazepam. In specific embodiments, the active agent is diazepam, while in other specific embodiments the active agent is not diazepam. In specific embodiments, the active agent is estazolam, while in other specific embodiments the active agent is not estazolam. In specific embodiments, the active agent is apomorphine, while in other specific embodiments the active agent is not apomorphine. In specific embodiments, the active agent is risperidone, while in other specific embodiments the active agent is not risperidone. In specific embodiments, the active agent is ketorolac, while in other specific embodiments the active agent is not ketorolac. In specific embodiments, the active agent is ibuprofen, while in other specific embodiments the active agent is not ibuprofen. In specific embodiments, the active agent is ketoprofen, while in other specific embodiments the active agent is not ketoprofen. In specific embodiments, the active agent is flurbiprofen, while in other specific embodiments the active agent is not flurbiprofen. In specific embodiments, the active agent is naproxen, while in other specific embodiments the active agent is not naproxen. In specific embodiments, the active agent is astemizole, while in other specific embodiments the active agent is not astemizole. In specific embodiments, the active agent is terfenadine, while in other specific embodiments the active agent is not terfenadine. In specific embodiments, the active agent is cimetidine, while in other specific embodiments the active agent is not cimetidine. In specific embodiments, the active agent is testosterone, while in other specific embodiments the active agent is not testosterone. In specific embodiments, the active agent is retin-A, while in other specific embodiments the active agent is not retin-A.

This examples of pharmaceutically active agents described herein is meant to be illustrative, not exhaustive.

In general, the pharmaceutically active agent may be present at a concentration typically used for that active agent in a topical formulation.

In some embodiments, the pharmaceutically active agent constitutes more than 25% of the first composition 21A. In some embodiments, the pharmaceutically active agent constitutes less than about 25% of the first composition 21A, such as from 0.1-25% (w/v), 0.1-20% (w/v), 0.1-15% (w/v), 0.1-10% (w/v), 0.1-5% (w/v), 0.1-1% (w/v), 0.5-25% (w/v), 0.5-20% (w/v), 0.5-15% (w/v), 0.5-10% (w/v), 0.5-5% (w/v), 0.5-1% (w/v), 1-25% (w/v), 1-20% (w/v), 1-15% (w/v), 1-10% (w/v), 1-5% (w/v), 5-25% (w/v), 5-20% (w/v), 5-15% (w/v), 5-10% (w/v), 10-25% (w/v), 10-20% (w/v), 10-15% (w/v), 15-25% (w/v), 15-20% (w/v) and 20-25% (w/v), including 0.1% (w/v), 0.5% (w/v), 1% (w/v), 5% (w/v), 10% (w/v), 15% (w/v), 20% (w/v or 25% (w/v). However, because the adherent properties of the compositions may provide extended drug exposure and/or controlled drug delivery, in some embodiments a lower concentration of the pharmaceutically active agent can be used while still achieving the desired pharmaceutical effect. In any event, the amount of the pharmaceutically active agent can be determined by the skilled artisan.

In specific embodiments, chlorhexidine gluconate is selected as the pharmaceutically active agent. In general, the chlorhexidine gluconate may be present at a concentration typically used in a topical formulation. In some embodiments, the chlorhexidine gluconate constitutes less than about 25% of the first composition 21A, such as from 0.1-25% (w/v), 0.1-20% (w/v), 0.1-15% (w/v), 0.1-10% (w/v), 0.1-5% (w/v), 0.1-1% (w/v), 0.5-25% (w/v), 0.5-20% (w/v), 0.5-15% (w/v), 0.5-10% (w/v), 0.5-5% (w/v), 0.5-1% (w/v), 1-25% (w/v), 1-20% (w/v), 1-15% (w/v), 1-10% (w/v), 1-5% (w/v), 5-25% (w/v), 5-20% (w/v), 5-15% (w/v), 5-10% (w/v), 10-25% (w/v), 10-20% (w/v), 10-15% (w/v), 15-25% (w/v), 15-20% (w/v) and 20-25% (w/v), including 0.1% (w/v), 0.5% (w/v), 1% (w/v), 2% (w/v), 3% (w/v), 4% (w/v), 5% (w/v), 10% (w/v), 15% (w/v), 20% (w/v) or 25% (w/v).

In specific embodiments, the amount of chlorhexidine gluconate in the first composition 21A is selected to provide a final pharmaceutical composition comprising chlorhexidine gluconate in a range of 0.1% to 5% (w/v) and the resin based tincture. Because the adherent properties of the compositions may provide extended drug exposure and/or controlled drug delivery, in some embodiments a lower concentration of chlorhexidine gluconate can be used while still achieving the desired pharmaceutical effect. In any event, the amount of chlorhexidine gluconate can be determined by the skilled artisan. Generally, the amount used will be within the range of +/−25% of the indicated concentration, such as within +/−10% of the indicated concentrations.

In some embodiments, such as embodiments directed to transmucosal delivery, the pharmaceutically active agent is present at a dose approved for clinical use and solubilized in a volume of 200 µl or less. In specific embodiments, such as specific embodiments directed to transmucosal delivery, the pharmaceutically active agent is solubilized in a volume of 25-200 µ.

In some embodiments, such as embodiments directed to topical or transdermal delivery, the pharmaceutically active agent is present in a dose approved for clinical use and solubilized in a volume of 2 ml or less. In specific embodiments, such as specific embodiments related to topical or transdermal delivery, the pharmaceutically active agent is solubilized in a volume of 1 ml or less.

Resin

As the resin, any topically and pharmaceutically acceptable resin may be used. For example, the resin may include, but is not limited to, naturally occurring resins and gums, such as those that are harvested from trees, although gum resins also may be prepared by synthetic means (see for example, U.S. Pat. Nos. 5,644,049, 5,429,590 and 4,307,717). Exemplary resins include benzoin resinous exudate harvested from Styracaceae trees, including Benzoin Siam from Styrax Tonkinesis and Benzoin Sumatra from Styrax Benzoin. Tincture of benzoin and benzoin compound tincture is readily available through numerous commercial sources, including many drug stores and suppliers of surgical goods. Another resin (i.e., resinous tree exudate) that may be utilized and is commonly used in the medical arts for enhancing the adherence of surgical bandages is mastic, a hard resin that is harvested from *Pistacia lentiscus*. Other resins that can be used include the gum resin exudates from Burserceae trees, including *Boswellia serrata* (also known as Boswellin), *Boswellia dalzielii, Boswellia carteri* (olibanum gum) and the oleoresin *Canarium luzonicum* or *Canarium commune* (Elemi gum or resin). Dammar, olibanum and myrrh gum also can be used in the resin. Oleoresins useful in the compositions of the invention include balsam resins. Additional resins (i.e., resinous exudates) contemplated from other tree species include *Eucalyptus* species (*Eucalyptus globulus*) and Myrtaceae "Tea-tree" species (*Melaleuca alternifolia, Leptospermum scoparium,* and *Kunzea ericoides*). Many naturally occurring resins have pharmaceutical properties, and their topical application may cause irritation in certain patients or exacerbate certain conditions. Prudent choice of the resins 21B to be used in preparing a particular pharmaceutical composition takes into consideration the disorder to be treated and the sensitivities of a particular patient's skin. In some embodiments, the resin is benzoin or mastic gum. In specific embodiments, the resin is benzoin. In some embodiments, a combination of resins can be used.

In one embodiment, the second ampoule 20B may consist of only the resin. In other embodiments, the second ampoule 20B may contain a second composition 21B comprising the resin, a second volatile solvent and water. In some embodiments, a combination of resins can be used in the second composition 21B.

In some embodiments, the second composition 21B does not include glycerin.

In some embodiments, the resin component constitutes more than 20% (w/v) of the second composition 21B. In other embodiments, the resin component constitutes about 20% (w/v) or less of second composition 21B. In specific embodiments, the resin component constitutes from about 1% (w/v) to about 30% (w/v), such as 1-25% (w/v), 1-20% (w/v), 1-15% (w/v), 1-10% (w/v), 1-5% (w/v), 2-30% (w/v), 2-25% (w/v), 2-20% (w/v), 2-15% (w/v), 2-10% (w/v), 2-5% (w/v), 3-30% (w/v), 3-25% (w/v), 3-20% (w/v), 3-15% (w/v), 3-10% (w/v), 3-5% (w/v), 5-30% (w/v), 5-25% (w/v), 5-20% (w/v), 5-15% (w/v), 5-10% (w/v), 10-30% (w/v), 10-25% (w/v), 10-20% (w/v), 10-15% (w/v), 15-30% (w/v), 15-20% (w/v), 16-24% (w/v) and 16-20% (w/v) of the second composition 21B.

In specific embodiments, the amount of resin in the second composition 21B is selected to provide a final pharmaceutical composition comprising where the concentration of the resin is in a range of 1% to 25% (w/v). In specific embodiments that may be particularly suitable for preparations to be applied to the skin, the resin is mastic gum and is present in a final concentration in the final pharmaceutical composition of from 1.5% to 15% (w/v), including from 1.5% to 5% (w/v), such as from 2.5% to 3.5% (w/v). In specific embodiments that may be particularly suitable for preparations to be applied to the mucosa, the resin is benzoin and is present in a final concentration in the final pharmaceutical composition of from about 5% to about 35%, such as from about 5% to about 20%, such as from about 5% to about 10%, such as from about 5% to about 8%, such as from about 15% to about 35%, including from 5% to 35%, from 5% to 20%, from 5% to 10%, from 5% to 8%, from 15% to 35%, including about 5%, about 8%, about 10%, about 15%, about 20%, about 35%, including 5%, 8%, 10%, 15%, 20%, and 35%.

Water

In the embodiments in which the first ampoule 20A contains a first composition 21A comprising the pharmaceutically active agent and water, the amount of water (v/v) in the first composition 21A is from about 1% to about 40%, such as from 5-40%, 10-40%, 20-40% or 30-40% of the first composition 21A, including 1%, 5%, 10%, 20%, 25%, 30%, or 40% of the first composition 21A.

In the embodiments in which the second ampoule 20B contains a second composition 21B comprising the resin and water, the amount of water (v/v) in the second composition 21B is from about 1% to about 40%, such as from 5-40%, 10-40%, 20-40% or 30-40% of the second composition 21B, including 1%, 5%, 10%, 20%, 25%, 30%, or 40% of the second composition 21B. If too much water is present, the resin may lose its biological activity or its characteristic resin properties.

In specific embodiments, the amount of water in the first composition 21A and the amount in the second composition 21B is selected to provide a final pharmaceutical composition comprising water is in a range of 1% to 40% (v/v), including water in a range of 1% to 25% (v/v), including a final amount of water of up to about 25% or up to about 40%, such as up to 25% or up to 40%. If too much water is present, the pharmaceutical composition may exhibit instability which may be observed, for example, by the formation of precipitates or the loss of intrinsic properties of the resin. The amount of water that can be present without the formation of unacceptable levels of precipitates may vary with the purity of the resin and/or the identity of the pharmaceutically active agent, and typically ranges from about 1% to about 25% (v/v) water.

As discussed above, in some embodiments, the pharmaceutically active agent is poorly soluble in a typical resin tincture composition comprising volatile solvent. In the context of the methods and compositions described herein, the presence and amount of water in the first composition 21A, if any, and the amount of water in the second composition 21B may be selected and controlled to address this issue. For example, in some embodiments, the presence and amount of water in the first composition 21A, if any, facilitates dissolution of the pharmaceutically active agent when mixed with the second composition 21B, which comprises the resin. In other embodiments, the presence and amount of water in the second composition 21B facilitates dissolution of the pharmaceutically active agent when mixed with the first composition 21A.

Additionally or alternatively, the presence and amount of water in the final pharmaceutical composition may be selected and controlled to create an environment in which the pH of the final pharmaceutical composition can be adjusted in order to promote a logD of the pharmaceutically active agent that is suitable or advantageous for transdermal or transmucosal delivery.

For example, for transdermal applications, a logD of about 1 or greater may facilitate or enhance transdermal delivery, such as by promoting diffusion through the stratum corneum into the epidermal and dermal layers of the skin. Thus, in some embodiments, such as embodiments for transdermal formulations applied topically to the skin, the presence and amount of water in the final pharmaceutical composition may be selected and controlled such that the pH can be adjusted such that the logD of the pharmaceutically active agent is about 1 or greater, about 2 or greater, about 3 or greater, or higher. For example, the pH of the final pharmaceutical composition may be adjusted to about 7.4 for fentanyl (logD of 3.97) or tretinoin (i.e., Retin-A) (logD of 4.19).

For transmucosal applications, a log D of about 1 or less may facilitate or enhance transmucosal delivery, such as by promoting diffusion through the mucosal membranes. Thus, in some embodiments, such as embodiments for transmucosal formulations applied to the mucosa, the presence and amount of water in the final pharmaceutical composition may be selected and controlled such that the pH can be adjusted such that the logD of the pharmaceutically active agent is about 1 or less, about 0 or less, about −1 or less, about −2 or less, or less. These parameters are exemplary, but non-limiting.

Volatile Solvent

As the volatile solvent(s), any pharmaceutically acceptable volatile solvent can be used for the volatile solvent(s) in the first composition 21A, if any, and for the volatile solvent(s) in the second composition 21B, such as ethyl acetate, n-propyl acetate, alcohols such as methanol, ethanol, propanol, and isopropanol, isopropyl alcohol, ketones, such as acetone, and ethers such as dimethyl ether. Other evaporative compounds may also find use, so long as they are compatible with other components of the pharmaceutical compositions and topically acceptable to the majority of patients. In specific embodiments, a volatile solvent in the first composition 21A, if any, and/or a volatile solvent in the second composition 21B is an alcohol such as ethanol, propanol, and isopropanol. In very specific embodiments, a volatile solvent in the first composition 21A and/or a volatile solvent in the second composition 21B is isopropanol. In some embodiments, the volatile solvent(s) in the first composition 21A, if any, is(are) the same as the volatile solvent(s) in the second composition 21B. In other embodiments, the volatile solvent(s) in the first composition 21A, if any, is(are) different from the volatile solvent(s) in the second composition 21B. In other embodiments a volatile solvent among a number of volatile solvents in the first composition 21A, if any, is the same as a volatile solvent among a number of volatile solvents in the second composition 21B. In other embodiments, a volatile solvent in the first composition 21A, if any, and/or a volatile solvent in a second composition 21B is an isopropyl alcohol mixture in water. In specific embodiments, a volatile solvent in the first composition 21A, if any, and/or a volatile solvent in a second composition 21B is a 70% isopropyl alcohol mixture in water.

In some embodiments, the amount of volatile solvent(s) in the second composition 21B is from about 60% to about 99% (v/v), including about 60% to about 95%, or about 60% to about 80%, or 60% to 80%, or 60% to 95%, including 60%, 70%, 80%, 90% 98% and 99% of the total first or second compositions 21A, 21B. The amount of volatile solvent(s) in first composition 21A, if any, may be similar, but is not particularly limited.

In some embodiments, such as compositions comprising chlorhexidine gluconate, the amount of volatile solvent(s) in the first and second compositions 21A and 21B is independently from about 40% to about 99% (v/v), including about 50% to about 95%, or about 60 to about 99%, or about 60% to about 80%, including 50% to 95%, or 60% to 80%, or 60% to 95%, 60% to 99%, including 40%, 40.2%, 50%, 60%, 70%, 80%, 90% and 99% of the total first or second composition. In specific embodiments, the amount of volatile solvent in the first composition 21A is 70% (v/v). In specific embodiments, the volatile solvent is isopropyl alcohol in an amount of 70% (v/v) in the first composition 21A.

In some embodiments, the relative amount of the volatile solvent(s) in the first composition 21A, if any, is substantially the same as, or the same as, the relative amount of the volatile solvent(s) in the second composition 21B. In other embodiments, the difference between the relative amount of volatile solvent(s) in the first composition 21A, if any, and second composition 21B is about 25% or less, about 20% or less, about 15% or less, about 5% or less, or about 1% or less, all w/v %. In specific embodiments, the difference between the relative amount of volatile solvent(s) in the first composition 21A, if any, and second composition 21B is 25% or less, 20% or less, 15% or less, 5% or less, or 1% or less, all w/v %. In specific embodiments, the relative amount of the volatile solvent(s) in each of the first composition 21A, if any, and the second composition 21B is independently from about 60% to about 80%, such as from 60% to 80%, all w/v %. For example, the first composition 21A, if any, may comprise 80% volatile solvent while the second composition 21B may comprise 60% volatile solvent (e.g., a difference of 20%). If the difference between the relative amount of solvent(s) in the first and second compositions is too great, precipitation of some pharmaceutically active agents may occur. In specific embodiments, the volatile solvent in both the first (if any) and second compositions is isopropyl alcohol. In other embodiments, the volatile solvent in both the first (if any) and second compositions is isopropyl alcohol, and combining the first and second compositions results in a final concentration of isopropyl alcohol of 70% (v/v).

In specific embodiments, the amount of volatile solvent in the first composition 21A, if any, and second composition 21B is selected to provide a final composition comprising volatile solvent(s) in a range of 60% to 99% (v/v).

Pharmaceutical Composition

The pharmaceutical composition (i.e., the mixture of the first and second compositions 21A and 21B) can be a sticky slurry or solution, which can be applied to a site on the skin, nail or a mucosal membrane, such as the buccal mucosal membrane. The consistency of the pharmaceutical composition can be varied by, for example, adjusting the relative amount of volatile solvent and resin. For areas where evaporation of the volatile solvent may be slower, such as mucosal membrane such as the gums, a composition with less volatile solvent may be advantageous. On the other hand, for areas that are hard to reach, such as between the toes, a composition with more volatile solvent may be advantageous. Still, for treatment of more severe lesions, such as due to athlete's foot infection, for example, a more viscous composition (with less volatile solvent) may be advantageous.

In some embodiments, the pharmaceutical composition does not include glycerin.

Optional Components

The pharmaceutical compositions optionally may include one or more other optional components, which may be provided in the first composition 21A within the first ampoule 20A, in the second composition 21B within the second ampoule 20B, or which may be provided within the interior 30 of the applicator tube 10 such that the optional components are added after the first and second compositions 21A and 21B are combined.

In some embodiments, the first composition includes fillers such as zinc oxide and microcrystalline cellulose.

In some embodiments, the pharmaceutical compositions include a penetration enhancer, i.e., a chemical compound that, when included in a formulation, temporarily increases the permeability of the skin to a drug allowing more of the drug to be absorbed in a shorter period of time. Examples of penetration enhancers that can be used include dimethylsulfoxide (DMSO), n-decyl methyl sulfoxide, N,N-dimethylacetamide, N,N-methyl-2-pyrrolidone and octylphenylpolyethylene glycols. In some embodiments, menthol and/or peppermint oil may function as enhancers. For example, menthol and/or peppermint oil have been shown to function as enhancers for nicotine, fentanyl, zolmitriptan and dihydroergotamine, when formulated in resin compositions as described herein (e.g., comprising resin and volatile solvent).

In some embodiments, the pharmaceutical compositions include one or more other pharmaceutically acceptable carriers. Advantageously, any additional carrier does not adversely affect the effectiveness of the pharmaceutically active agent or the resinous delivery vehicle and does not damage the application site. Suitable pharmaceutical carriers include sterile water; saline, dextrose; dextrose in water or saline; condensation products of castor oil and ethylene oxide combining about 30 to about 35 moles of ethylene oxide per mole of castor oil; liquid acid; lower alkanols; oils such as corn oil; olive oil, peanut oil, sesame oil, wintergreen oil, lanolin oil and the like, with emulsifiers such as mono- or di-glyceride of a fatty acid, or a phosphatide, e.g., lecithin, and the like; glycols; polyalkylene glycols; aqueous media in the presence of a suspending agent, for example, sodium carboxymethyl-cellulose; sodium alginate; poly(vinyl pyrrolidone); and the like, alone, or with suitable dispensing agents such as lecithin; polyoxyethylene stearate; and the like.

Optionally, the composition as a whole or the other carrier may also contain adjuvants such as preserving, stabilizing, wetting, emulsifying agents and the like.

Optionally, the composition may include dyes, fragrances, flavors, and other topically and pharmaceutically acceptable components. In some embodiments, the use of a dye permits easy determination/verification of where the composition has been applied, such as to permit easy determination/verification that the composition has been applied to the entire target site, such as a site being prepared for surgery, or any other site where treatment with the pharmaceutically active agent is desired, such as any other site where the pharmaceutically active agent is being applied to prevent (or reduce the risk of) or treat infection.

Suitable dyes useful for this purpose are known in the art and include triarylmethane dyes (e.g., gentian violet, crystal violet, ethyl violet, and brilliant green), monoazo dyes (e.g., FD&C Yellow No. 5 and FD&C Yellow No. 6), diazo dyes (e.g., D&C Red No. 17), indigoid dyes (e.g., FD&C Blue No. 2), xanthene dyes (e.g., FD&C Red No. 3), anthraquinone dyes (e.g, D&C Green No. 6), quinoline dyes (e.g., D&C Yellow No. 1), and FD&C dyes (e.g., FD&C Blue No. 1 and FD&C Green No. 3). See, e .g., U.S. Pat. No. 8,231,602.

Suitable dyes can also include Cape Aloe.

In some embodiments, the compositions as described herein contain more than one dye. In specific embodiments, the compositions contain FD&C Yellow No. 5, FD&C Yellow No. 6, and FD&C Blue #2. In other embodiments, the compositions contain FD&C Yellow No. 5, and FD&C Yellow No. 6.

In some embodiments, such as where the composition comprises chlorhexidine gluconate, the composition does not include an indigoid dye, such as FD&C Blue No. 2.

In some embodiments, the second composition 21B includes from about 0.1% to about 1% (w/v), or from about 0.1% to about 0.8% (w/v), or from about 0.1% to about 0.5% (w/v) or from about 0.1% to about 0.2% (w/v), or from about 0.2% to about 1% (w/v), or from about 0.2% to about 0.8% (w/v), or from about 0.2% to about to about 0.5% (w/v), or from about 0.5% to about 1% (w/v), or from about 0.5% to about 0.8% (w/v), or from about 0.8% to about 1% (w/v) of the dye, including 0.1-1% (w/v), 0.1-0.8% (w/v), 0.1-0.5% (w/v), 0.1-0.2% (w/v), 0.2-1% (w/v), 0.2-0.8% (w/v), 0.2-0.5% (w/v), 0.5-1% (w/v), 0.5-0.8% (w/v) and 0.8-1% (w/v) of the dye, such as 0.1% (w/v), 0.2% (w/v), 0.5% (w/v), 0.8% (w/v) and 1% (w/v) of the dye.

For example, the dye can be dissolved in water and then combined with a volatile solvent (such as any described above) to prepare a composition comprising about 55-85% (v/v) volatile solvent and about 15-45% water, such as 15%, 20%, 25%, 30%, 40% or 45% water. Then, the dye composition can be added to the second composition 21B before it is added to the first composition 21A. Alternatively, the dye composition can be added after the first and second compositions 21A and 21B are combined to form the pharmaceutical composition.

Additionally or alternatively, the second composition 21B can be treated with a base or acid, such as NaOH or HCl, to achieve an optimal pH to maximize the anti-bacterial property of chlorhexidine gluconate. In specific embodiments, the pH is from about 5.5 to about 7.0, including from about 6.0 to about 7.0, including from 5.5 to 7.0, including from 6.0 to 7.0. In other specific embodiments, the final pH of the pharmaceutical composition is from about 5.5 to about 7.0, including from about 6.0 to about 7.0, including from 5.5 to 7.0, including from 6.0 to 7.0. In other specific embodiments, the base or acid concentration is 1-10 N. In other specific embodiments, the base or acid is added to the second composition 21B after the dye is added to the second composition 21B.

Blister Package

The dual chamber applicator 100 may be placed inside a blister package 50 and sealed, for example, with Tyvek lidding prior to sterilization. The blister package 50 may be composed, for example, of a clear PVC base film. Only an exterior surface of the applicator tube 10 is rendered sterile (i.e., not the contents of the first and second ampoules 20A and 20B) such that the blister package 50 may be opened aseptically and used in a sterile field. A plurality of dual chamber applicators 100 may be connected in series with perforations between each blister package 50 to permit easy separation.

Method of using the Dual Chamber Applicator to Effect Topical, Transdermal or Transmucosal Delivery of the Active Agent The dual chamber applicator 100 may be used for topical, transdermal or transmucosal delivery of medication. Prior to opening the blister package 50, the first and the second ampoules 20A and 20B are broken by applying pressure on the blister package 50. The blister package 50 is opened to remove the dual chamber applicator 100. The dual chamber applicator 100 is shaken to allow the first composition 21A (containing the pharmaceutically active agent) and the second composition 21B (containing the resin) to mix within the interior 30 of the applicator tube 10 to form the pharmaceutical composition. In some embodiments, the first and second compositions 21A and 21B are mixed together for about one minute. In other embodiments, the first and second compositions 21A and 21B are mixed together for about less than one minute, such as from about 10 to about 60 seconds, or from about 10 to about 50 seconds, or from about 10 to about 40 seconds, or from about 10 to about 30 seconds, or from about 10 to about 20 seconds, or from about 15 to about 60 seconds, or from about 15 to about 50 seconds, or from about 15 to about 40 seconds, or from about 15 to about 30 seconds, or from about 15 to about 20 seconds, or from about 20 to about 60 seconds, or from about 20 to about 50 seconds, or from about 20 to about 40 seconds, or from about 20 to about 30 seconds, or from about 40 to about 60 seconds, or from about 30 to about 50 seconds, or from about 30 to about 40 seconds, or from about 40 to about 60 seconds, or from about 40 to about 50 seconds, or from about 50 to about 60 seconds, including from 10-60 seconds, 10-50 seconds, 10-40 seconds, 10-30 seconds, 10-20 seconds, 15-60 seconds, 15-50 seconds, 15-40 seconds, 15-30 seconds, 15-20 seconds, 20-60 seconds, 20-50 seconds, 20-40 seconds, 20-30 seconds, 30-60 seconds, 30-50 seconds, 30-40 seconds, 40-60 seconds, 40-50 seconds and 50-60 seconds. In specific embodiments, the first and second compositions 21A and 21B are mixed together for one minute or 10, 15, 20, 30, 40 or 50 seconds.

The pharmaceutical composition may then be applied, for example, topically by squeezing the applicator tube 10 and pressing the applicator device 40 to a surface upon which the user intends to deliver the pharmaceutical composition (i.e., the medicine).

In specific embodiments, the pharmaceutical composition may form a film on the site of application, after application and evaporation of the volatile solvent(s). These embodiments may achieve extended retention of the pharmaceutically active agent on the site of application because the film is resistant to water and abrasion. By forming a film, the number of applications required for the pharmaceutically active agent to effectively treat the condition may be reduced. In addition, this sustained application is beneficial in many situations, such as in the use of compositions comprising anti-infection agents on surgical sites, pain relief, or therapy of a persistent condition. Additionally, many dermatological conditions are exacerbated by moisture, so the water-repellent qualities of the film offer particular advantages in that context by protecting the application site from moisture that may cause further damage. Nevertheless, the films can be conveniently and easily removed, for example with alcohol or washing or rinsing, when desired. Thus, the pharmaceutical compositions described herein can be formulated for direct application to a site needing treatment (such as a lesion or surgical site), and can be left in place for an extended period of time, without requiring a conventional adhesive bandage.

After allowing the film to dry for approximately 20-30 seconds, dressing or tape may be placed on the area to which the film was applied.

EXAMPLES

The inventive compositions having being generally described, it will be more readily understood by reference to the following examples which are included for purposes of illustration only and are not intended to limit the present invention.

Example 1

A dual chamber applicator can be made by forming an applicator tube having a first sealed end and a second open end. Two ampoules can be inserted into the applicator tube. The ampoules can be cut and sealed at one end, filled with the desired contents, and flame sealed. One ampoule can contain a first composition comprising or consisting of a pharmaceutically active agent and optionally a first volatile solvent and/or water. The pharmaceutically active agent may be selected, for example, from one of the pharmaceutically active agents described above. Another ampoule can contain a second composition comprising a resin, a second volatile solvent, and water. The resin may be selected, for example, from one of the pharmaceutically active agents described above. The ampoules can be sterilized. After the ampoules are inserted, an applicator device having a porous structure can be inserted into the open end of the applicator tube to control the flow of the pharmaceutical composition out of the applicator tube. In particular, the applicator device can allow passage of the pharmaceutical composition to permit its application, while simultaneously preventing passage of portions of the ampoules. The dual chamber applicator can be sterilized. The dual chamber applicator can be inserted into a blister package.

Example 2

The dual chamber applicator of Example 1 may be used for topical, transdermal or transmucosal delivery of medication. The ampoules provided within the dual chamber applicator can be crushed to release the contents of the ampoules to an interior of the applicator tube. A user can shake the dual chamber applicator for a predetermined period of time (e.g., thirty seconds) to mix the first composition (containing the pharmaceutically active agent) with the second composition (containing the resin) to form a pharmaceutical composition. The dual chamber applicator can be squeezed and the pharmaceutical composition (i.e., the medicine) can be applied to a mucosal site or a skin site via the applicator device.

Example 3

First Composition
A first composition is prepared that consists of a pharmaceutically active agent (alone), or that comprises a pharmaceutically active agent and optionally, a first volatile solvent and/or water Second Composition
A second composition is prepared by combining a resin and a volatile solvent to a mixing vessel and stirring the mixture for about several hours or overnight. If not stirred overnight, the stirred time can be from about 3-6 hours, 3-5 hours, 3-4 hours, or 4 hours. After settling for about an hour, the resulting solution is decanted into another vessel. The settling time may be about 1 hour.

The supernatant is decanted or the particulate removed using a cheesecloth. The supernatant is then filtered twice, first at 5 microns and then at 0.45 microns. The filtering can be performed using a syringe filter, including a syringe nylon filter. The amount of volatile solvent lost due to evaporation while settling is calculated, and this amount is added to the solution in the vessel.

Water is added to the filtered solution. The mixture is then filtered, which can be accomplished using a syringe filter, including a syringe nylon filter, a 5-micron syringe nylon filter and/or a 0.45-micron syringe nylon filter. If too much water is added, the adhesive characteristics and biological activity of the resin can be diminished after the solution is filtered.

Alternatively, to prepare the second composition, resin is mixed with isopropyl alcohol and water, followed by filtering sequentially at 5 microns and then at 0.45 microns, which can be accomplished using a syringe filter, including a syringe nylon filter.

Depending on the pharmaceutically active agent selected (such as for nicotine, diclofenac, ondansetron or sildenafil), the pH of the second composition is raised to greater than 6.1 before the first and second compositions are combined, such as by adding 1-10 N NaOH. If a precipitate forms at about pH 6.1, it can be removed by letting the second composition settle and then filtering. For example, the second composition may be allowed to settle for a period of time such as one week, and then the resulting supernatant may be filtered, such as using a 0.45 micron filter. Then the pH may be adjusted (increased) further as desired.

Optionally, dye and water are separately mixed until the dye is dissolved, and volatile solvent is added and mixed to produce a dye solution. The dye solution and the second composition are combined with water and mixed overnight. The dye/second composition is filtered, such as on a large or small scale. The filter can be a syringe filter, including a syringe nylon filter, a 5-micron syringe nylon filter or a 0.45-micron syringe nylon filter.

The first ampoule 20A is cut and sealed at one end, filled with the first composition 21A, and flame sealed. The second ampoule 20B is cut and sealed at one end, filled with the second composition 21B, and flame sealed. The first and second ampoules 20A and 20B are placed within the applicator tube 10, and the applicator device 40 is inserted into the open end of the applicator tube 10. The first and second ampoules 20A and 20B may be crushed to allow the first and second compositions 21A and 21B to mix and form a pharmaceutical composition for topical, transdermal or transmucosal delivery. Equal volumes of the first composition 21A and the second composition 21B may be combined by simple mixing over a period of about 15 to about 30 seconds.

Example 4

First Composition

Chlorhexidine gluconate and a first volatile solvent are added to a first mixing vessel and stirred to produce a first composition.

Second Composition

A resin and a volatile solvent are added to a second mixing vessel and stirred for about several hours to produce a solution. The stirred time can be from about 3-6 hours, 3-5 hours, 3-4 hours, or 4 hours. After settling for at least an hour, the solution is decanted into another vessel. The settling time may be about 1 hour, several hours or overnight. The amount of volatile solvent lost due to evaporation while settling is calculated, and this amount is added to the solution in the vessel. Water is added and the resulting (second) mixture is filtered to produce a tincture. The filter can be a syringe filter, including a syringe nylon filter, a 5-micron syringe nylon filter, a 0.45-micron syringe nylon filter or any filter used in large scale mass production. This mixture is allowed to settle for a period, usually 12-48 hours, to allow the supernatant to completely clarify. At this point, there is a clear partition between the supernatant and an underlying, denser, organic liquid phase. The supernatant is then carefully decanted or otherwise separated from the underlying liquid so that the liquid does not mix with the supernatant.

Dye and water are separately mixed until the dye is dissolved, and volatile solvent is added and mixed to produce a dye solution comprising 15-45% (v/v) water. The dye solution and the tincture solution are combined with water and mixed overnight to form the second composition. The second composition is filtered and allowed to settle. The filter can be a syringe filter, including a syringe nylon filter, a 5-micron syringe nylon filter, a 0.45-micron syringe nylon filter or any filter used in large scale mass production. After settling, the pH of the second composition may adjusted, such as by using 1-10 N NaOH or HCl, to achieve a pH that supports the antimicrobial activity of chlorhexidine gluconate, such as a pH of from about 5.5 to about 7.0, including from about 6.0 to about 7.0, including from 5.5 to 7.0, including from 6.0 to 7.0.

The first ampoule 20A is cut and sealed at one end, filled with the first composition 21A, and flame sealed. The second ampoule 20B is cut and sealed at one end, filled with the second composition 21B, and flame sealed. The first and second ampoules 20A and 20B are placed within the applicator tube 10, and the applicator device 40 is inserted into the open end of the applicator tube 10. The first and second ampoules 20A and 20B may be crushed to allow the first and second compositions 21A and 21B to mix and form a pharmaceutical composition for topical, transdermal or transmucosal delivery. Equal volumes of the first composition 21A and the second composition 21B may be combined by simple mixing over a period of about 15 to about 60 seconds. The final composition comprises up to 25-40% (v/v) water.

Example 5

Chlorhexidine gluconate is commercially available from Xttrium Laboratories (Mt. Prospect, Ill.) in a 20% (w/v) solution in water (20 mL of the solution contains 4 g of chlorhexidine gluconate).

First Composition

A first composition is prepared by adding 20 mL of the 20% chlorhexidine gluconate solution to 10 mL of water and 70 mL of 100% isopropyl alcohol, resulting in a chlorhexidine gluconate concentration of 4% (w/v) in 70% (v/v) isopropyl alcohol.

Second Composition

A second composition is prepared by adding 160 g benzoin to 497.5 mL isopropyl alcohol and stirring overnight. After settling for about an hour in the morning, the supernatant is removed either by using a cheesecloth or by decanting. The supernatant is filtered twice, first at 5 microns and then at 0.45 microns. The filtering can be performed, such as on a large or small scale, using a syringe filter, including a syringe nylon filter. Isopropyl alcohol is added to the filtered solution to make up for the amount of volatile solvent lost due to evaporation while settling.

213.5 mL of deionized water is added to the filtered solution and the second composition is stirred for 1 hour, and the emulsion is left to settle overnight. The solution is allowed to settle until the supernatant clarifies and there is a clear partition between the overlying supernatant and the underlying, denser, organic liquid phase. The partitioned (water-containing) supernatant is decanted and filtered, such as with a syringe filter, including a syringe nylon filter, a 5-micron syringe nylon filter and/or a 0.45-micron syringe nylon filter.

Alternatively, the second composition is prepared by mixing benzoin with isopropyl alcohol and water, followed by filtering the resulting mixture sequentially at 5 microns and then at 0.45 microns, which can be accomplished using a syringe filter, including a syringe nylon filter.

The filtered solution is brought up to 711 mL with 70% (v/v) isopropyl alcohol, bringing the content of benzoin to 22.5% (w/v).

A dye solution is produced by mixing 4.688 g. FD&C Yellow #5, 2.839 g. FD&C #6 and 0.516 g. FD&C Blue #2 for a total of 8 g. The mixture is then combined and mixed with 85.2 ml of water until the dyes are solubilized. The solubilized mixture is then mixed with 198.8 ml of isopropyl alcohol, followed by filtering the resulting mixture sequentially at 5 microns and then at 0.45 microns. The filtering can be accomplished using a syringe filter, including a syringe nylon filter.

Alternatively, 284 mL of 70% (w/v) isopropyl alcohol is added to the 8 g dye mixture and stirred for 1 hour. The stirred dye mixture is left to settle overnight, followed by decanting of the supernatant and filtering of the supernatant sequentially at 10 microns and 0.45 microns. The filtered dye solution is brought up to 284 mL with 70% (w/v) isopropyl alcohol, bringing the content of the dye to 2.8% w/v in the alcohol.

Alternatively, the dye solution is then mixed with the mixture overnight and subsequently filtered at 0.45 microns and brought up to 1 L with 70% (v/v) isopropyl alcohol.

The second composition is stored at room temperature, 30° C. or 40° C. in containers to prevent evaporation and checked monthly for precipitation or other evidence of instability.

To form the final pharmaceutical composition, the second composition is allowed to settle for 1 month at room temperature, and its pH is adjusted to a pH of 6.5 using 10 N NaOH.

The first ampoule 20A is cut and sealed at one end, filled with the first composition 21A, and flame sealed. The second ampoule 20B is cut and sealed at one end, filled with the second composition 21B, and flame sealed. The first and second ampoules 20A and 20B are placed within the applicator tube 10, and the applicator device 40 is inserted into the open end of the applicator tube 10. The first and second ampoules 20A and 20B may be crushed to allow the first and second compositions 21A and 21B to mix and form a pharmaceutical composition for topical, transdermal or transmucosal delivery. The second composition 21B may be combined with the first composition 21A in equal volumes by simple mixing over a period of about 15 to about 30 seconds.

Example 6

First Composition

A first composition is prepared by adding chlorhexidine gluconate to isopropyl alcohol (IPA) such that the mixture is 100 mL with 4% chlorhexidine gluconate in 70% (v/v) IPA at pH 6.5.

Second Composition

A second composition is prepared by adding 800 grams of benzoin resin to 1.972 L of 100% IPA and filtered. 100% IPA is then added to the filtered solution make up for loss of volume during the filtering.

845 mL of deionized water is added to the filtered solution and subsequently filtered with a 0.45 micron filter. 70% (v/v) IPA is then added to make up for loss of volume during the filtering.

The pH of the filtered solution is brought to between about 6.0 and 7.0 by adding 10N NaOH, in order to provide for a final benzoin concentration of 5% (w/v) or 8% (w/v). One or both of 100% and 70% (v/v) IPA is added to the pH-adjusted solution to provide a final benzoin mixture.

Taking 71.6 mL of the benzoin mixture, add 21.3 mL of dye (prepared by mixing 4.688 grams FD&C Yellow No. 5 and 0.284 grams FD&C Yellow No. 6; adding 70% IPA to reach a volume of 284 mL; filtering the mixture at 0.45 microns; and bringing the volume back up to 284 mL with 70% IPA) and 7.1 mL of 70% (v/v) IPA.

The benzoin/dye mixture is refrigerated overnight. The resulting supernatant is then decanted while cold and 70% (v/v) IPA is added to the supernatant to bring the volume up to 100 mL to arrive at the second composition. The second composition is allowed to stand overnight at room temperature to equilibrate.

The first ampoule 20A is cut and sealed at one end, filled with the first composition 21A, and flame sealed. The second ampoule 20B is cut and sealed at one end, filled with the second composition 21B, and flame sealed. The first and second ampoules 20A and 20B are placed within the applicator tube 10, and the applicator device 40 is inserted into the open end of the applicator tube 10. The first and second ampoules 20A and 20B may be crushed to allow the first and second compositions 21A and 21B to mix and form a pharmaceutical composition for topical, transdermal or transmucosal delivery. The first and second compositions 21A and 21B may be stored in their respective flame sealed ampoules in the dark at room temperature until use.

Example 7

A first composition is prepared with the following components:
60%-80% (v/v) isopropyl alcohol;
20%-40% (v/v) water; and
4% (w/v) chlorhexidine gluconate.

A second composition is prepared with the following components:
60%-80% (v/v) isopropyl alcohol;
20%-40% (v/v) water;
16%-20% (w/v) resin; and
0.2%-0.8% (w/v) dye.

The first ampoule 20A is cut and sealed at one end, filled with the first composition 21A, and flame sealed. The second ampoule 20B is cut and sealed at one end, filled with the second composition 21B, and flame sealed. The first and second ampoules 20A and 20B are placed within the applicator tube 10, and the applicator device 40 is inserted into the open end of the applicator tube 10. The first and second ampoules 20A and 20B may be crushed to allow the first and second compositions 21A and 21B to mix and form a pharmaceutical composition for topical, transdermal or transmucosal delivery.

Example 8

Pharmaceutical compositions comprising vardenafil or sildenafil mesylate as the pharmaceutically active agent and benzoin gum as the resin based tincture were prepared along the lines described in Example 1, with the following components:

Vardenafil (free base) (10 mg/75 μL) at 13.3% (w/v); 20% (w/v) benzoin gum in 79% (w/v) ETOH /21% (w/v) water; 2% (v/v) peppermint oil; pH=4.1.

Sildenafil Mesylate: 25 mg/75 μL at 25% (w/v); 20% (w/v) benzoin gum in 79% (w/v) ETOH/21% (w/v) water; 5%(w/v) L-methanol; 2% (w/v) peppermint oil; 0.1% (v/v) sucralose; pH=5.2.

Technical and scientific terms used herein have the meanings commonly understood by one of ordinary skill in the art to which the present invention pertains, unless otherwise defined. Reference is made herein to various methodologies known to those of ordinary skill in the art. Publications and other materials setting forth such known methodologies to which reference is made are incorporated herein by reference in their entireties as though set forth in full. Any suitable materials and/or methods known to those of ordinary skill in the art can be utilized in carrying out the present invention. However, specific materials and methods are described. Materials, reagents and the like to which reference is made in the following description and examples are obtainable from commercial sources, unless otherwise noted.

As used herein, the singular forms "a," "an," and "the" designate both the singular and the plural, unless expressly stated to designate the singular only. Likewise, singular forms of terms designate both the singular and plural, unless expressly stated to designate the singular only. For example, "active agent" means "active agent" or "active agents."

The term "about" in connection with numerical values and ranges means that the number comprehended is not limited to the exact number set forth herein, and is intended to refer to ranges substantially within the quoted range while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10%, plus or minus 5%, or plus or minus 1%, of the particular term.

The phrase "substantially free" as used herein generally means that the described composition (e.g., pharmaceutical composition, etc.) comprises less than about 5%, less than about 3%, or less than about 1%, by weight, based on the total weight of the composition at issue, of the excluded component.

As used herein, the phrases "therapeutically effective amount" and "therapeutic level" mean that drug dosage or plasma concentration in a subject, respectively, that provides the specific pharmacological response for which the drug is administered in a subject in need of such treatment. It is emphasized that a therapeutically effective amount or therapeutic level of a drug will not always be effective in treating the conditions/diseases described herein, even though such dosage is deemed to be a therapeutically effective amount by those of skill in the art. For convenience only, exemplary dosages, drug delivery amounts, therapeutically effective amounts and therapeutic levels are provided below with reference to adult human subject. Those skilled in the art can adjust such amounts in accordance with standard practices as needed to treat a specific subject and/or condition/disease.

As used herein, the term "skin" refers to the membranous tissue forming the external covering or integument of an animal and consisting in vertebrates of the epidermis and dermis.

As used herein, the term "nail" refers to a substructure, composed mainly of the protein keratin, of the outer layer of the skin. As such, "nail" includes both "fingernails" and "toenails" of an animal. The "nail bed" is the skin on the top of which the nail grows.

As used herein, the term "mucosa" refers to mucous membrane epithelium, including oral mucous membranes including buccal mucous membranes.

One versed in the art would appreciate that there may be other embodiments and modifications within the scope and spirit of the disclosure. Accordingly, all modifications attainable by one versed in the art from the present disclosure, within its scope and spirit, are to be included as further embodiments of the present disclosure.

What is claimed is:

1. A dual chamber applicator for applying a medicine comprising a pharmaceutically active agent to a mucosal site or skin site, comprising:
    an elongated tube having a sealed end and an open end;
    a first ampoule disposed in the elongated tube and containing a first composition comprising a pharmaceutically active agent and a first volatile solvent, water, or a combination thereof;
    a second ampoule disposed in the elongated tube and containing a second composition comprising a resin based tincture, a second volatile solvent and water,
    the first composition configured to combine with the second composition within the elongated tube to form a medicine to be delivered to a mucosal site or a skin site; and
    an applicator device provided at the open end of the elongated tube, the applicator device configured to control flow of the medicine out of the open end of the elongated tube and deliver the medicine via topical, transdermal or transmucosal delivery,
    wherein the applicator device comprises a porous structure configured to allow passage of the medicine to be delivered to the mucosal site or the skin site, while simultaneously preventing passage of ruptured portions of the first and second ampoules or particulates from the resin based tincture that did not dissolve into solution, and
    wherein an average pore size of the porous structure ranges from 1 μm to 300 μm.

2. The dual chamber applicator of claim 1, wherein the first and second ampoules are non-concentric.

3. The dual chamber applicator of claim 1, wherein a length of the second ampoule is greater than a length of the first ampoule.

4. The dual chamber applicator of claim 1, wherein the first composition further comprises a second pharmaceutically active agent, different from the pharmaceutically active agent.

5. The dual chamber applicator of claim 1, wherein the second composition further comprises a second resin based tincture, different from the resin based tincture.

6. The dual chamber applicator of claim 1, wherein the pharmaceutically active agent is selected from the group consisting of bacitracin, polymyxin, chlorhexidine gluconate, fentanyl, retinoic acid (Retin-A), zolmitriptan, sumatriptan, naratriptan, rizatriptan, lorazepam, and mupirocin.

7. The dual chamber applicator of claim 1, wherein the pharmaceutically active agent is selected from the group consisting of ondansetron, granisetron, zolmitriptan, dihydroergotamine, sumatriptan, rizatriptan, fentanyl, cocaine, alprazolam, clonazepam, lorazepam, diazepam, estazolam, apomorphine, risperidone, buprenorphine, naloxone, flumazenil, tadalafil, vardenafil, sildenafil, sildenafil mesylate, dolasetron, palonsetron, triazolam, naratriptan, diclofenac, etololac, meclofenamate, indocin, meloxicam, nabumetone, oxaprozin, prioxicam, sulindac, tolmetin, celecoxib, loratadine, desloratidine, cetirizine, morphine, hydromorphine, levorphanol, meperidine, oxycodone, oxymorphone, propanolol, calcitriol, and methylphenidate.

8. The dual chamber applicator of claim 1, wherein the pharmaceutically active agent is selected from the group consisting of nicotine, scopolamine, lidocaine, benzocaine, ketorolac, ibuprofen, ketoprofen, flurbiprofen, naproxen, astemizole, terfenadine, cimetidine, testosterone, retin-A.

9. The dual chamber applicator of claim 1, wherein the resin based tincture is selected from the group consisting of mastic gum and benzoin.

10. The dual chamber applicator of claim 1, wherein the first composition comprises chlorhexidine gluconate, the first volatile solvent, and 1-40% (v/v) water, the second composition comprises mastic gum, the second volatile solvent and 1-40% (v/v) water, and a final amount of water in the medicine is up to 40% (v/v).

11. The dual chamber applicator of claim 1, wherein the pharmaceutically active agent comprises bacitracin and the resin based tincture comprises mastic gum.

12. The dual chamber applicator of claim 1, wherein the first composition and the second composition do not contain glycerin.

13. The dual chamber applicator of claim 1, wherein the first volatile solvent, the second volatile solvent or a combination thereof are independently selected from the group consisting of ethyl acetate, n-propyl acetate, methanol, ethanol, propanol, isopropanol, isopropyl alcohol, acetone and dimethyl ether.

14. The dual chamber applicator of claim 1, provided in a blister package configured to receive the dual chamber applicator in an interior of the blister package and be sealed prior to sterilization.

15. The dual chamber applicator of claim 14, prepared by a process comprising:
  disposing the dual chamber applicator in the blister package;
  sealing the blister package; and
  sterilizing the blister package such that the blister package and an exterior surface of the elongated tube are sterilized.

16. The dual chamber applicator of claim 1,
  wherein a viscosity of the medicine is 10 to 30 centipoise, and
  wherein the average pore size of the porous structure ranges from 1 µm to 100 µm.

17. The dual chamber applicator of claim 1,
  wherein a viscosity of the medicine is 30 to 500 centipoise, and
  wherein the average pore size of the porous structure ranges from 40 µm to 300 µm.

18. The dual chamber applicator of claim 1, wherein a pore volume of the porous structure is less than or equal to 80%.

19. The dual chamber applicator of claim 1, wherein the first composition is more stable against precipitation and degradation of the pharmaceutically active agent than the medicine.

20. The dual chamber applicator of claim 19, wherein the pharmaceutically active agent is selected from bacitracin and chlorhexidine gluconate.

21. A method for delivery of a medicine comprising a pharmaceutically active agent to a mucosal site or a skin site using a dual chamber applicator including an elongated tube having a sealed end and an open end, a first ampoule and a second ampoule disposed within the elongated tube, the first ampoule containing a first composition comprising a pharmaceutically active agent and a first volatile solvent, water, or a combination thereof, and the second ampoule containing a second composition comprising a resin based tincture, a second volatile solvent, and water, and an applicator device provided at the open end of the elongated tube, the method comprising:
  deforming the elongated tube to crush the first and second ampoules to release the first composition and the second composition into an interior of the elongated tube;
  shaking the dual chamber applicator such that the first composition and the second composition combine to form the medicine to be delivered to the mucosal site or the skin site; and
  applying the medicine topically, transdermally or transmucosally via a porous structure of the applicator device configured to allow passage of the medicine to be delivered to the mucosal site or the skin site, while simultaneously preventing passage of ruptured portions of the first and second ampoules or particulates from the resin based tincture that did not dissolve into solution, wherein an average pore size of the porous structure ranges from 1 µm to 300 µm.

22. The method of claim 21, wherein the pharmaceutically active agent comprises chlorhexidine gluconate and the resin based tincture comprises mastic gum such that crushing the first and second ampoules and shaking the dual chamber applicator forms a medicine comprising chlorhexidine gluconate and mastic gum.

23. The method of claim 21, wherein the pharmaceutically active agent comprises bacitracin and the resin based tincture comprises mastic gum such that crushing the first and second ampoules and shaking the dual chamber applicator forms a medicine comprising bacitracin and mastic gum.

24. The method of claim 21, wherein the first composition is more stable against precipitation and degradation of the pharmaceutically active agent than the medicine.

25. The method of claim 24, wherein the pharmaceutically active agent is selected from bacitracin and chlorhexidine gluconate.

* * * * *